US008758381B2

(12) United States Patent
Kuhr et al.

(10) Patent No.: US 8,758,381 B2
(45) Date of Patent: Jun. 24, 2014

(54) LANCET DEVICE WITH OPTIONALLY REUSABLE LANCETS STORED IN A MAGAZINE

(75) Inventors: Hans-Juergen Kuhr, Mannheim (DE); Michael Keil, Limburgerhof (DE); Hans List, Hesseneck-Kailbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 19 days.

(21) Appl. No.: 13/308,141

(22) Filed: Nov. 30, 2011

(65) Prior Publication Data
US 2012/0143235 A1 Jun. 7, 2012

(30) Foreign Application Priority Data
Dec. 4, 2010 (EP) ..................................... 10015297

(51) Int. Cl.
*A61B 17/32* (2006.01)
(52) U.S. Cl.
USPC ......................................................... 606/181
(58) Field of Classification Search
USPC ........... 606/181, 182, 183; 600/583; 141/181, 141/182, 183
See application file for complete search history.

(56) References Cited

U.S. PATENT DOCUMENTS

| | | | | |
|---|---|---|---|---|
| 4,794,926 A * | 1/1989 | Munsch et al. | ................ | 606/183 |
| 6,228,100 B1 * | 5/2001 | Schraga | .......................... | 606/183 |
| 6,616,616 B2 * | 9/2003 | Fritz et al. | ...................... | 600/583 |
| 7,150,755 B2 * | 12/2006 | Levaughn et al. | ............ | 606/181 |
| 7,223,276 B2 | 5/2007 | List et al. | | |
| 7,678,127 B2 * | 3/2010 | Trissel et al. | ................. | 606/183 |
| 8,002,785 B2 | 8/2011 | Weiss et al. | | |
| 8,221,332 B2 * | 7/2012 | Robbins et al. | ............... | 600/583 |
| 2005/0149089 A1 * | 7/2005 | Trissel et al. | ................. | 606/181 |
| 2006/0161078 A1 | 7/2006 | Schraga | | |
| 2006/0282109 A1 | 12/2006 | Jansen et al. | | |
| 2007/0016104 A1 | 1/2007 | Jansen et al. | | |
| 2007/0299458 A1 | 12/2007 | Epple | | |
| 2008/0082023 A1 * | 4/2008 | Deck et al. | ..................... | 600/583 |
| 2009/0012428 A1 * | 1/2009 | Kramer et al. | ................ | 600/583 |
| 2010/0094172 A1 * | 4/2010 | List et al. | ....................... | 600/583 |
| 2010/0130997 A1 * | 5/2010 | Levaughn et al. | ............ | 606/172 |
| 2010/0185120 A1 * | 7/2010 | Sacherer et al. | ............. | 600/583 |
| 2011/0160759 A1 * | 6/2011 | Schraga et al. | ............... | 606/172 |

FOREIGN PATENT DOCUMENTS

| | | |
|---|---|---|
| DE | 100 22 720 | 11/2001 |
| DE | 103 26 692 | 2/2005 |
| EP | 1 384 438 | 1/2004 |
| WO | WO 03/071940 | 9/2003 |
| WO | WO 2006/027101 | 3/2006 |
| WO | WO 2009/067269 | 5/2009 |

* cited by examiner

*Primary Examiner* — Thomas McEvoy
*Assistant Examiner* — Julie A Szpira
(74) *Attorney, Agent, or Firm* — Bose McKinney & Evans LLP (57) ABSTRACT

An inventive lancet device for producing a puncture wound, in particular for collecting a sample of a body fluid which has a magazine holder for a lancet magazine containing a plurality of lancets. The lancet device can be alternatively operated such that either a new lancet is used for each puncture process by automatically advancing the lancet magazine stepwise or the automatic stepwise advance of the lancet magazine can be suppressed or deactivated so that, if desired, several punctures can be carried out with the last used lancet before an unused lancet is used at a desired time.

23 Claims, 7 Drawing Sheets

LANCET DEVICE WITH OPTIONALLY REUSABLE LANCETS STORED IN A MAGAZINE

RELATED APPLICATIONS

This application claims priority to EP10015297.4, filed Dec. 4, 2010 which is hereby incorporated herein by reference in its entirety.

BACKGROUND

The present invention concerns a lancet device for producing a puncture wound, in particular for collecting a sample of a body fluid. The lancet device has a magazine holder for a lancet magazine containing a plurality of lancets and can be alternatively operated such that either a new lancet is used for each puncture process by automatically advancing the lancet magazine stepwise or the automatic stepwise advance of the lancet magazine can be suppressed so that, if desired, several punctures can be carried out with the last used lancet before an unused lancet is used at a desired time.

The present invention additionally concerns a withdrawal system for withdrawing a sample of a body fluid comprising a lancet device as mentioned above and a matching lancet magazine containing several lancets.

Lancets which can be inserted into the appropriate body part to produce a puncture wound are usually used to withdraw a small amount of a body fluid such as e.g. blood from a suitable body part such as for example from a finger pad or earlobe for analytical or diagnostic purposes. Blood withdrawal systems which consist of a lancet device and appropriately adapted lancets suitable for such an application are well-known. Such lancet devices usually comprise a housing in which a lancet drive is located which moves the lancet mechanically for insertion into the selected skin area.

Nowadays, high demands are made on lancet devices with regard to producing a minimal pain sensation on the one hand, as well as simplicity in operation, compact design as well as cost-effective manufacture and economical operating costs on the other hand. The main focus is on a simple and comfortable operation of the lancet device which is especially important for diabetics who must frequently and regularly determine their blood sugar level by self-monitoring. In this connection, easy handling and low pain burden often result in a greater willingness of the patients to comply with this requirement and thus to support the success of the therapy.

An important advance in this regard is the use of lancets stored in a magazine i.e. lancets contained in a magazine. Such lancet magazines contain a plurality of lancets and can be inserted into the magazine holder of a corresponding lancet device. This makes it unnecessary to frequently insert or replace individual lancets which is a considerable facilitation in particular for diabetes patients with limited dexterity or eyesight. Accordingly, the demand for lancet devices with lancets stored in a magazine is increasing. The use of lancets stored in a magazine or lancet magazines in lancet devices usually requires a mechanism to advance or step the magazine forward which enables an unused lancet to be brought into use after a puncture process. However, it has turned out that even when using lancets stored in a magazine and the corresponding lancet devices it may also be desirable especially for economical reasons to use the stored lancet repeatedly if desired.

Accordingly, a lancet device is described in U.S. Pat. No. 8,002,785 which can hold a lancet magazine containing several lancets and which has a magazine advancing mechanism which enables the lancet magazine to be advanced in such a manner that the lancets stored therein can be successively coupled to a push rod of the lancet drive. The lancet drive is mechanically decoupled from the magazine advancing mechanism and the lancet device has an actuating element which allows the magazine advancing mechanism to be actuated independently of the lancet drive and in particular independently of the tensioning device. This enables the user to at any time exchange an already used lancet for an unused lancet by actuating the magazine advancing mechanism. However, a disadvantage of this system is that the magazine advancing mechanism in every case requires an active handling by the user which can result in an already used lancet being undesirably often used by forgetting to actuate the magazine advancing mechanism.

U.S. Publication No. 2006/0161078 A1 discloses a circular disk-shaped cassette for a test device as well as a test method using the said test device with the cassette. The cassette comprises a plurality of lancet needles as well as a plurality of test strips and a mechanism for linkage to the test device. Since each test element can only be used once, the cassette must be advanced stepwise either manually or automatically e.g. by means of an electric drive after a test process or puncture has been carried out.

Special lancing aids with a circular disk-shaped lancet magazine are also disclosed in U.S. Publication No. 2007/0299458 A1 where the lancets are each arranged radially facing outwards in the direction of puncture. The lancing aids have a mechanism which prevents intentional or accidental reuse of an already used lancet. This is achieved by means of the fact that in each tensioning process of the lancet drive the lancet magazine is rotated further such that a lancet that is as yet unused comes into contact with the lancet drive and additionally the replaceable lancet magazine has a lock to prevent the reinsertion of used magazines.

International Publication No. WO 2009/067269 A1 concerns a lancing aid with a replaceable circular disk-shaped magazine which comprises a plurality of lancets. The device has an anti-reverse mechanism so that the magazine can only be advanced in one direction thus preventing reuse of an already used lancet. Moreover, a mechanism is disclosed which enables one or more of the previously used lancets to be used again in an emergency. In order to preclude an accidental or improper use, the used up lancet magazine must if necessary be removed from the lancing device but in any case manually turned back against the actual direction of rotation.

SUMMARY

Embodiments described herein provide a lancet device which enables the withdrawal of a small amount of a body fluid, preferably blood, and largely avoid the respective disadvantages of the prior art.

In particular, lancet devices in accordance with these teachings are generally easy to operate, provide protection against undesired side-effects such as, e.g., infections, enable already used lancets to be used repeatedly, if desired, but in doing so ensure that only the last used lancet in each case can be reused and if required can be used independently of the availability of consumables such as unused lancet magazines.

In one embodiment, a lancet device for producing a puncture wound is provided. It comprises a magazine holder for a lancet magazine with several lancets; a lancet drive with a drive spring, a tensioning device for tensioning the drive spring and a connecting element which can be brought into contact with a lancet arranged in the lancet magazine and which, by means of the lancet drive, can move the lancet that has been brought into contact with it for a puncturing movement in order to produce a puncture wound; a magazine advancing mechanism which allows the lancet magazine to be advanced in such a manner that the lancets stored therein can be successively brought into contact with the connecting element and which has an active and a passive operating state; and a selection element with which the magazine advancing mechanism can be selectively shifted into the active or into the passive operating state. In the active operating state the magazine advancing mechanism automatically advances the lancet magazine before or after a puncturing movement of a lancet such that an as yet unused lancet of the lancet magazine is brought into contact with the connecting element of the lancet device in the subsequent puncturing movement. In the passive operating state the automatic magazine advancing mechanism is deactivated such that the lancet magazine is not advanced before or after a puncturing movement of a lancet so that in the subsequent puncturing movement the same lancet as in the previous puncturing movement is again brought into contact with the connecting element of the lancet drive.

One aspect of this disclosure concerns a lancet device for producing a puncture wound which is suitable for collecting small volume samples of a body fluid for diagnostic purposes. Examples of such body fluids are blood or interstitial fluid but preferably blood. The lancet device taught herein, which is often also referred to as a lancing aid, is suitable for multiple use and has a magazine holder for a lancet magazine with several lancets.

The lancet magazine for insertion into the magazine holder is suitable for holding and storing a plurality of lancets and usually 2 to 50, as a rule 2 to 25, preferably 3 to 10, particularly preferably 4 to 8 and especially preferably 6 to 8 and most preferably 6 lancets. The magazine usually comprises a magazine housing which at least partially surrounds the lancets and at least one exit opening to allow the active lancet tip to emerge. The lancet magazine preferably has a segmented configuration where in each case one lancet is stored in one segment also referred to in the following as a lancet holder, preferably spatially separated from the other lancets. In this embodiment it is advantageous when each of the segments has its own exit opening for the lancets stored therein.

The spatial arrangement of the lancet magazine is not subject to any fundamental limitations but should advantageously be aligned to the design or shape of the corresponding magazine holder or lancet device. It is basically possible to use various forms of magazines familiar to a person skilled in the art, for example, drum magazines, flat magazines, stack magazines, tape magazines, belt magazines and so forth. Against this background it has proven to be advantageous when the lancet magazine is designed to be rotationally symmetric for example in the form of a disk or preferably in the form of a drum.

The lancet magazines then have an axis of rotation which advantageously runs parallel to the device axis of the lancet device or may even be identical to this axis, especially in the case of the aforementioned drum magazines. Moreover, it may also be advantageous when the axis of rotation is essentially aligned perpendicular to the device axis especially of an aforementioned disk magazine. The term device axis is understood in this case to mean an axis which runs substantially parallel to the puncture direction of the respective lancet and typically runs through the distal or proximal end of the lancet device. Within the scope of a preferred embodiment the lancet magazine designed in the form of a drum is a so-called revolver magazine in which the individual lancets are each aligned parallel to the axis of rotation of the drum magazine.

In this case the plurality of lancets is preferably located in lancet holders of the lancet magazine arranged in a ring.

The magazine holder of the lancet device can be advantageously designed such that a lancet magazine as described above can be inserted therein and mechanically connected to the lancet device. In addition to the magazine holder, the lancet device usually additionally has a housing with an exit opening wherein the exit opening can also be provided with a cap belonging to the housing. The housing has an interface which is accessible to the user from the outside which is also referred to in the following as user interface. Within the scope of a further embodiment the cap surrounds a lancet magazine inserted into the magazine holder and can thus close the magazine holder. Furthermore, the cap can be connected to a mechanism for adjusting the puncture depth for example in a rotatably mounted form connected via a thread to the remaining housing.

The lancet device additionally has a lancet drive comprising a drive spring, a tensioning device for tensioning the drive spring and a connecting element. The connecting element can be brought into contact with a lancet arranged in the lancet magazine, typically arranged in an active position, and, by means of the lancet drive, can move the lancet that has been brought into contact with it in order to produce a puncture wound. The connecting element can be configured as a push rod which together with a lancet coupled thereto can be moved at high speed by means of the lancet drive in such a manner that a puncturing movement, preferably a puncture and retraction movement can be carried out. Such a mechanism is disclosed in International Publication No. WO/2006/027101 to which reference in this regard is herewith made.

The drive spring provided as part of the lancet drive can be configured in any form that appears suitable to a person skilled in the art, for example, as a leaf spring or as a spiral spring which, for example, can be tensioned by stretching, compression or twisting. The drive spring is tensioned by means of a tensioning device which usually comprises an actuating element which interacts with the tensioning device in such a manner that upon actuation thereof the drive spring is tensioned preferably when the actuating element is pressed down.

Within the scope of another exemplary embodiment, the lancet drive comprises a drive rotor that can be driven by the drive spring and a coupling mechanism on the drive side which converts a rotational movement of the drive rotor into a translational movement of the push rod in the advancing phase of the lancet drive and by means of the drive rod converts this into a puncturing movement of the lancet.

In this embodiment, the tensioning device includes a rotatable tensioning rotor which braces the end of the drive spring that faces away from the drive rotor. This tensioning rotor can be rotated in order to tension the drive spring in the same rotational direction in which the drive rotor rotates during the forward movement phase while the rotation of the drive rotor is blocked. During the forward movement phase the tensioning rotor is locked against a backwards rotation so that, after release of the blocking, the drive rotor performs a rotational movement which is converted into a translational movement of the push rod. The drive rotor advantageously rotates through a total rotational angle range of 360° during one work cycle.

The tensioning device is actuated by a rotary-slide-transmission which cooperates with an actuating element in the manner described above and is advantageously formed by a cam in the form of a peripheral double groove on the tensioning rotor and two control pins of the tensioning sleeve which travel along the cam when the actuating element is pressed down. A drive mechanism of this type is disclosed in European Patent No. EP 1 384 438 A1 to which reference is herewith made in this regard. The type of drive is one of a large number of possible types of drives which are familiar to a person skilled in the art and which can be used.

The lancet device additionally has a magazine advancing mechanism with which the lancet magazine can be advanced in such a manner that the lancets stored in it can be successively brought into an active position and thus into contact with the connecting element and which has an active and a passive operating state. The term magazine advancing mechanism is understood in this context as a mechanism which allows an as yet unused lancet among the plurality of lancets located in the lancet magazine to be brought into contact with the connecting element and thus indirectly with the lancet drive following an already used lancet. This process in which an already used lancet is replaced by an as yet unused lancet from the same lancet magazine in such a manner that the as yet unused lancet is located in a position in which it can be brought into contact with the connecting element or preferably can be coupled to the said connecting element, is referred to herein as advancing or also as stepwise advancing of the lancet magazine. Thus, a linearly constructed lancet magazine in which the individual lancets are arranged next to one another or one behind the other can for example be advanced by displacement. In exemplary embodiments in which the plurality of lancets are arranged in a rotationally symmetrical, for example disk-shaped or drum-shaped lancet magazine as described above in a radial or axial alignment, advancing or stepwise advancing is carried out by rotation around the rotational axis of the magazine where the angle of rotation is usually determined by the number of lancets in the magazine or the distance between them.

An exemplary embodiment therefore concerns a lancet device for producing a puncture wound comprising a magazine holder for a lancet magazine with several lancets; a lancet drive with a drive spring, a tensioning device for tensioning the drive spring and a connecting element which can be coupled to a lancet arranged in the lancet magazine and which, by means of the lancet drive, can be moved together with a lancet coupled thereto to make a puncturing movement in order to produce a puncture wound; a magazine advancing mechanism which allows the lancet magazine to be advanced in such a manner that the lancets stored therein can be successively coupled to the connecting element and which has an active and a passive operating state, and a selection element with which the magazine advancing mechanism can be selectively shifted into the active or into the passive operating state.

In the active operating state the magazine advancing mechanism automatically advances the lancet magazine before or after a puncturing movement of a lancet such that an as yet unused lancet of the lancet magazine is coupled to the connecting element in the subsequent puncturing movement and wherein in the passive operating state the automatic magazine advancing mechanism is deactivated such that the lancet magazine is not advanced before or after a puncturing movement of a lancet so that in the subsequent puncturing movement the same lancet as in the previous puncturing and retraction movement is again coupled to the connecting element.

The magazine advancing mechanism has an active and a passive operating state according to exemplary embodiments. In this connection the term active operating state is understood to mean that the magazine advancing mechanism automatically advances the lancet magazine before or after a puncturing movement of a lancet such that an as yet unused lancet of the lancet magazine is brought into contact with the connecting element of the lancet drive in the subsequent puncturing movement. In this connection an automatic advance is one in which a separate operating step by the user of the lancet device is not necessary to advance the lancet magazine. This can for example be achieved in that the magazine advancing mechanism is mechanically coupled to the lancet drive. This coupling can for example be designed such that when the lancet drive is tensioned for example as described above when the actuating element is pressed down, the magazine that is inserted in each case is simultaneously advanced. This type of automatic magazine advance is described for example in International Publication No. WO/2003/071940. Alternatively the residual energy of the puncturing movement can be used to advance the magazine as described for example in German Patent No. DE 10022720 A1. In both cases no separate operating steps by the user would be necessary for advancing and before each puncture a new as yet unused lancet would be automatically brought into contact with the connecting element of the lancet drive.

The term "before or after a puncturing movement" is to be understood herein in connection with the advancing of the magazine to mean that the advancing of the lancet magazine takes place either before, preferably directly before the start of the puncture movement of a lancet or not until after, preferably directly after completion of the puncturing movement. In this connection the terms before or after refer to the respective operating cycle of the lancet device in which it is firstly tensioned and then triggered. Subsequently, a puncturing movement of the lancet that has been brought each time into contact with the lancet drive takes place, which after reaching the maximum excursion of the lancet in the puncture direction changes into a retraction movement. An advancing after a puncturing movement can in this connection be understood as an advancing of the magazine after completion of the puncture and retraction movement of a lancet as well as preferably an advancing directly after a puncturing movement. In the latter case the magazine can also be advanced completely or partially during the retraction movement of a lancet.

Moreover, it is also advantageous within the scope of these teachings when the magazine that is used at any one time, in particular an inserted drum magazine, can only be advanced until the last as yet unused lancet has been brought into contact with the connecting element of the lancet drive has been used. This prevents lancets that have already been used several times, possibly a long time in the past, from being reused intentionally or unintentionally.

Furthermore, it may be advantageous especially in the case of a magazine being advanced before a puncturing movement when the intended magazine can only be used in a predefined orientation and the first position of the lancet magazine is either empty or equipped with a place holder instead of a lancet. Alternatively it is also possible especially in the case of drum or disk magazines to bring the lancet located in the first position into contact with the lancet drive at the end of the cycle. Otherwise in this case it would not be possible to use the lancet provided at a first position of the magazine.

As used herein, the term passive operating state is generally understood to mean that the automatic magazine advancing mechanism is deactivated. As a consequence, the lancet magazine is not advanced before or after a puncturing movement of the lancet such that the same lancet as in the previous puncturing movement is again brought into contact with the connecting element of the lancet drive in the subsequent puncturing movement. This can be achieved analogously to the automatic stepwise advance described above by decoupling the magazine advancing mechanism mechanically from the lancet drive or from the tensioning mechanism and by means of the fact that a tensioning of the lancet device or the triggering of a puncture process does not also result in the lancet magazine being advanced. Hence, in this passive operating state a lancet that has been brought once into contact with the connecting element is used further in subsequent puncturing movements until the lancet magazine has been advanced or advanced stepwise.

The lancet device additionally has a selection element with which the magazine advancing mechanism can be selectively shifted into the active or into the passive operating state. In an exemplary embodiment, the selection element is designed such that the magazine advancing mechanism can in each case be reversibly shifted into the active or passive operating state. This can ensure that the lancet device can be selectively switched into the operating state desired in each case according to the current requirements of the user. Thus, it is for example possible to provide the lancet device with a preset operating state as a standard operating state which can then if desired be shifted by the user temporarily or permanently into the other respective operating state. In one embodiment, the lancet device is provided in such a manner that the magazine advancing mechanism is in an active operating state so that the magazine advancing mechanism automatically advances the lancet magazine before or after a puncturing movement of a lancet so that in the subsequent puncturing movement an as yet unused lancet of the lancet magazine is brought into contact with the connecting element of the lancet drive. This operating state can be interrupted or converted into the passive operating state by actuating the selection element such that the lancet magazine is not advanced before or after a puncturing movement of a lancet and as a result the same lancet as in the previous puncture and retraction movement is again brought into contact with the connecting element of the lancet drive in the subsequent puncturing movement.

The technical design of the selection element provided is not subject to any basic limitations and can be realized in the lancet device according to these teachings in a variety of ways. However, the selection element is typically designed such that it takes into account the dimensions of a lancet device that is usually operated manually and is readily accessible for the user. In one embodiment, the selection element is arranged on the operating interface of the lancet device and can be actuated manually. This ensures that the selection element is accessible to the user from outside and for example does not have to be firstly opened or dismantled. Conversely it may also be advantageous when the selection element is arranged such that it can only be accessed when the user firstly carries out a further action such as opening a cover thus, substantially excluding an accidental actuation of the selection element. However, the selection element is preferably mounted on the operating interface and is accessible from the outside of the lancet aid. In turn it is preferred that the selection element is arranged at a position on the operating interface in which it cannot be accidently actuated during operation in the intended manner preferably single-handed operation. For example the selection element can also be mounted in a depression of the operating interface that is accessible from outside. The selection element is preferably positioned on the operating interface such that the lancing aids can only be used while simultaneously actuating the selection element by using both hands.

The selection element can be designed such that, after actuating the selection element, the magazine advancing mechanism is shifted into the selected operating state until the other operating state is selected by further actuation of the selection element. This configuration can for example be realized by a switch which provides two switch positions such as for example a toggle switch with two positions of the tiltable switching element (on/off switch) or also a slide that can be moved into two positions. However, in this connection the construction must ensure that the respectively selected switch remains in the desired position after actuation so that the operating state desired in each case remains permanently.

However, it is alternatively also possible to design the selection element such that the magazine advancing mechanism can only be shifted from one of the two operating states into the other respective operating state during actuation of the selection element. This should for example then be the case if the selection element were to return automatically, i.e. without further action of the user, into the initial state after actuation. A possible technical design for this would for example be characterized in that the selection element is designed as a push-button with a return spring. In turn the said push-button would preferably be located at a position on the lancet device preferably at a position on the operating interface at which it would be difficult to simultaneously operate the selection element together with the operating element of the lancet device with one hand, which would preferably only be possible using both hands.

In one exemplary embodiment, the lancet device is provided such that the magazine advancing mechanism is in a preset active operating state. Additionally, the magazine advancing mechanism in this embodiment can only be shifted into the passive operating state while the selection element is actuated by for example pressing a push-button with a return spring designed as described above. This is a particularly advantageous embodiment of the lancet device because in this case the active operating state can only be deactivated by an active intervention which is usually not accidental during use, but the lancet device automatically falls back again into the active operating state that is intended as the standard setting. This ensures that multiple use of a lancet does not take place accidentally but rather only by a purposeful actuation of the selection element during each use of the lancet device.

The passive operating state of the lancing aid is characterized in that the automatic magazine advancing mechanism is deactivated. In this connection the term deactivated must be construed in a broad sense and can for example mean that the mechanism provided in each case for advancing the magazine is interrupted or alternatively is bypassed. The two possibilities differ essentially in that an interruption of the magazine advancing mechanism temporarily disables it, whereas it continues to operate in the case of bypassing but no longer causes the lancet magazine to advance. This can for example be accomplished by mechanically decoupling the lancet advancing mechanism from the lancet magazine in the passive operating state.

A further embodiment of the lancet device is characterized in that the magazine advancing mechanism is mechanically coupled to the lancet drive. In this connection a mechanical coupling is understood to mean that when the lancet drive is actuated preferably as part of an actuation of the tensioning device, some of the force exerted is used to advance the lancet magazine. For example when the tensioning device is actuated by pressing down the actuating element as described above, the magazine advancing mechanism is also actuated so that the lancet magazine is advanced and a new, as yet unused lancet is brought into contact with the connecting element of the lancet drive. One embodiment of the lancet device is accordingly characterized in that in the active operating state the magazine advancing mechanism is coupled to the tensioning device in such a manner that the lancet magazine is advanced during actuation of the tensioning device to tension the drive spring. The lancet magazine is then advanced as described above directly before the puncturing movement.

Alternatively, the advancing of the lancet magazine can also be coupled to the lancet drive or the tensioning device in such a manner that the residual energy of the lancet drive that still remains after a puncturing and retracting movement of a lancet is transferred onto the magazine advancing mechanism so that the lancet magazine is advanced and thus a new lancet is made available directly after a puncturing movement and optionally during the retracting movement of the lancet.

However, the lancet device of this disclosure is typically designed such that the magazine advancing mechanism is mechanically coupled to the lancet drive only in the active operating state. In the passive operating state the magazine advancing mechanism is accordingly preferably mechanically decoupled from the lancet drive and, as described above, the decoupling is preferably reversible and particularly preferably only persists during actuation of the selection element or persists until the lancet advancing mechanism is restored into the active operating state by actuation of the selection element. As described above the decoupling is preferably designed such that the magazine advancing mechanism is only bypassed i.e. it continues to operate but no longer advances the lancet magazine.

Such a mechanical coupling can for example be realized by a so-called step-switching mechanism. An exemplary embodiment therefore concerns a lancet device which is characterized in that the lancet advancing mechanism comprises a step-switching mechanism. Step-switching mechanisms as such are known to a person skilled in the art and are for example used in the construction of film projectors in which the film has to be advanced stepwise, and also in clock construction. However, other translational or rotational movements of objects can in principle be stepped using a step-switching mechanism. A step-switching mechanism is usually characterized in that it has a gripping mechanism which performs a periodic constantly repeated movement that is uniform for each repetition. This gripping mechanism is usually brought into mechanical engagement with a counter structure or a counter element of the body to be moved or rotated. In this process the periodic movement of the gripping element is converted into a stepped movement, preferably the rotation of the body to be moved.

Accordingly a further embodiment of the lancet device is characterized in that the step-switching mechanism comprises a movable gripper as well as several counter elements, where the movable gripper is arranged such that it can be engaged with the counter elements resulting in an advance of the lancet magazine. An advantageous embodiment of such a device is characterized in that the movable gripper of the step-switching mechanism is a component of the lancet device. In the context of this advantageous embodiment it is in turn preferred that the counter elements provided for engagement with the movable gripper on the device side are components of the lancet magazine. This disclosure therefore also concerns within the context of this embodiment a lancet device as described above which also comprises a lancet magazine where the lancet magazine may have counter elements which are arranged such that they can be brought into engagement with the movable gripper of a step-switching mechanism provided on the device side which enables the lancet magazine to be advanced.

In addition it is also possible in an alternative embodiment that counter elements of the step-switching mechanism are not directly arranged on the lancet magazine to be advanced but rather on a movable magazine carrier which is, e.g., located in the magazine holder of the lancet device. The magazine carrier provided within the scope of this embodiment can be designed such that it can be mechanically firmly but detachably connected to a lancet magazine as described above. Advancing the magazine for example by displacement or preferably in the case of a rotationally symmetric lancet magazine by rotation can then also be accomplished by displacing or rotating the magazine carrier that is also mounted in the device. In this case it is also advantageous when the movable magazine carrier has the counter elements of the step-switching mechanism which are intended to be brought into engagement with the movable gripper. An exemplary embodiment of the lancet device is accordingly characterized in that the magazine holder comprises a movable magazine carrier where the counter elements of the step-switching mechanism are a component of the movable magazine carrier. With respect to a reduced overall size which is desirable for lancet devices of the present type as well as with regard to a reduced proportion of components it is, however, advantageous to provide the counter elements of the step-switching mechanism as described above on the lancet magazine and to arrange the movable gripper on the device side such that it can be directly brought into engagement with these elements.

The step-switching mechanism that is typically provided allows, in an advantageous manner, the magazine advancing mechanism to be merely bypassed in the passive operating state as described above. This can for example be achieved in that the movable gripper of the step-switching mechanism does not engage with the counter elements in the passive operating state of the magazine advancing mechanism. For example the movable gripper can be displaced by switching on the passive operating state such that it continues to execute its recurring uniform gripping movement but no longer engages with the counter elements of the step-switching mechanism. This can for example take place by means of a temporary reversible rotation or displacement of the step-switching mechanism but preferably only of the movable gripper. For example the movable gripper of the step-switching mechanism can be displaced by means of or during an actuation of the selection element such that it would no longer engage with the counter elements as a result of which the advancing of the lancet magazine during the actuation or depending on the design, until the selection element is actuated again, would be interrupted. This could ensure that a magazine advance intended to be automatic could only be intentionally and specifically interrupted. This would provide the user of a lancet aid of these teachings with a high degree of flexibility with maximum safety due to automatic advancing and at all times enable the potentially desirable reuse of an already used lancet.

A further aspect of these teachings concerns a withdrawal system for withdrawing a sample of a body fluid comprising a lancet device as described previously and a suitable lancet magazine therefor with several lancets, wherein the embodiments described in each case also represent exemplary features of the disclosed withdrawal system. Accordingly the lancet magazine in this case can be a rotationally symmetric magazine and in particular a drum-shaped magazine as described above. The lancet drive also may comprise a step-switching mechanism in the context of this aspect. Also within the context of this aspect the counter elements of a step-switching mechanism provided on the instrument side can be mounted on the lancet magazine.

The lancet device taught herein makes it possible to prevent emergency situations in which a user has to take a blood sample for example in order to measure the blood glucose level, but does not have a reserve magazine on hand when the lancet store has been used up. In this case further use of the lancing aid would no longer be possible with an active automatic magazine transport until a new magazine had been inserted. The possibility of bypassing the advancing mechanism, however, allows the last lancet to be reused and thus at short notice ensures that the lancing aid can be used further.

A further improvement to operating safety and hygiene could be achieved when the system is coupled with a protection against reinsertion or reuse of used magazines and magazines that have already been removed. Such a protection against reinsertion for lancet magazines is described for example in U.S. Pat. No. 7,785,338 (Kuhr et al.).

Finally the lancet device taught herein provides great flexibility with regard to individual user habits which are often regional in character. For example the taught lancet device enables a variable presetting of the lancing aid by the manufacturer in the active or passive operating state which allows one to respond to specific user habits. In this connection it is in particular advantageous when the selection element is covered or provided with further safety elements.

BRIEF DESCRIPTION OF THE DRAWINGS

Further details and advantages are elucidated in more detail in the following on the basis of an embodiment example. In this connection the same reference numerals refer to the same or functionally identical elements or elements which correspond to one another with regard to their function. The principle of operation of the step-switching mechanism that is typically provided is elucidated in more detail on the basis of a disk-shaped lancet magazine but is not limited thereto and can be equally implemented with other forms of magazines such as for example drum magazines, flat magazines, stack magazines, tape magazines, belt magazines or other magazine forms. The described features can be used individually or in combination in order to create preferred embodiments.

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of these teachings.

Figure 1:
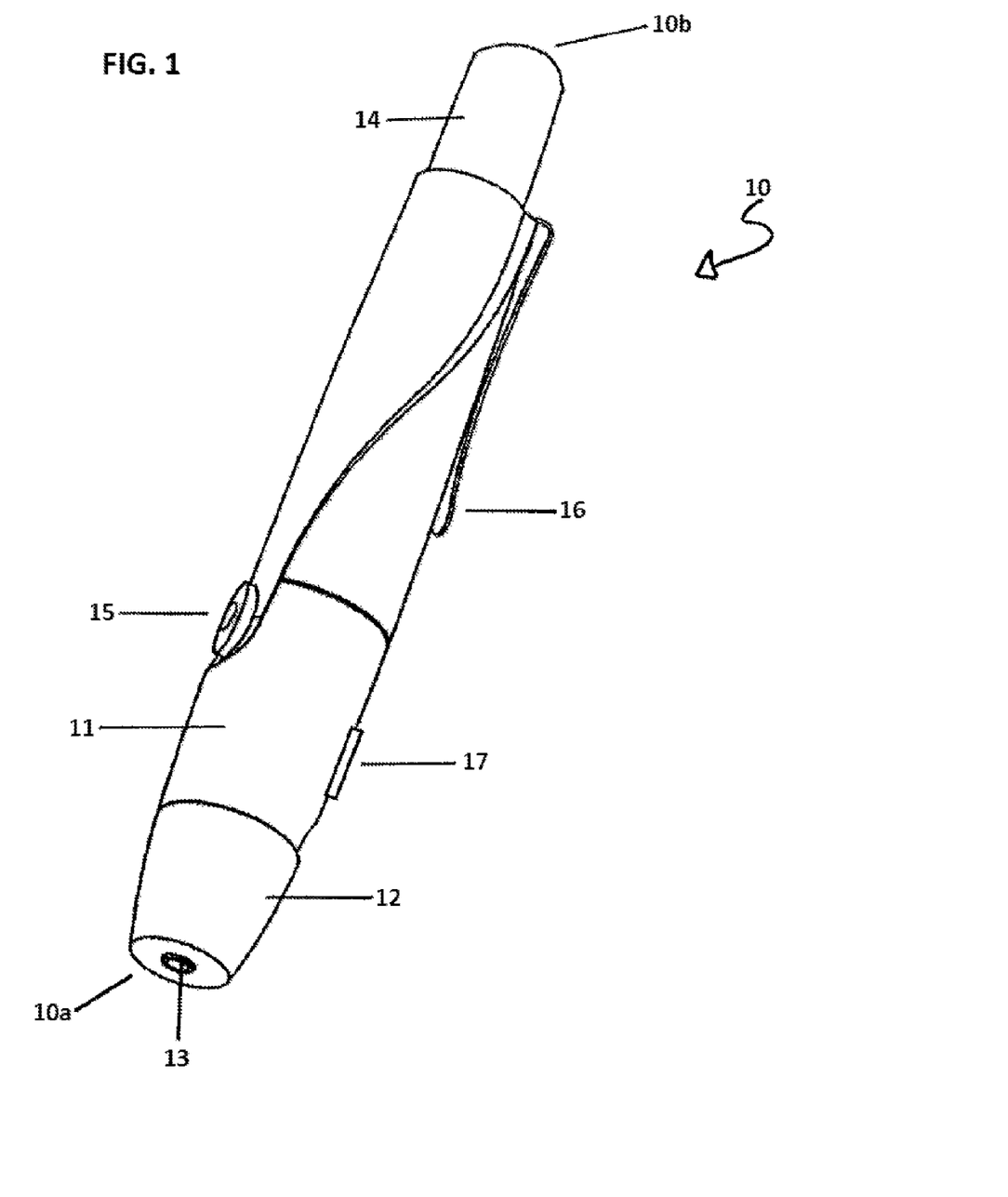
FIG. 1 shows a lancet device with a selection element in a perspective side view.

FIG. 1 shows a lancet device (10) with a selection element (17) in a perspective side view. The lancet device (10) shown as an example has a proximal end (10a) and a distal end (10b) as well as an approximately spindle-shaped housing or an approximately rotationally symmetric housing (11) with regard to a main axis of the device. The housing (11) in turn has an operating interface which faces outwards or is accessible from outside to a user as well as an attachment clip (16) for attaching the lancet device for example in order to fasten it to the clothing of a user when not in use. The main axis of the device passes through the proximal contact surface of the lancing aid (10) which when used as intended faces towards the body part to be punctured. A removable cap (12) which usually seals a hollow space (not shown) that is suitable for holding a lancet magazine is attached to the proximal end (10a) of the lancing aid (10) within the context of the present example. As shown in FIG. 1 the cap (12) has in turn an exit opening (13) at its proximal end, i.e. on its contact surface, through which a lancet moved in the puncture direction can emerge from the housing of the lancet device in order to produce a puncture wound in the body part to be punctured. The exit opening (13) can in this case be arranged centrally (as shown in FIG. 1) as well as off center on the contact surface of the cap (12) depending on the design of the intended lancet magazine.

The lancing aid (10) shown in FIG. 1 additionally has a selection element (17) which is mounted on the outside i.e. on the user interface of the housing (11) in the present example. In the form shown in FIG. 1 it can be designed as a slide which can be moved into two positions by means of which one of the two operating states described above can be selected either permanently or temporarily. Alternatively, it is also possible to design the selection element (17) in the form of a press switch or push-button. In particular in the embodiment as a push-button it is then suitable for temporarily activating an operating state which for example lasts until the selection element (17) which is designed as a push-button is pushed. Alternatively the selection element (17) can also be designed as a toggle switch or other suitable designs as described above. The selection element (17) shown as an example in FIG. 1 is attached to the operating interface of the housing (11) and in this form is accessible to the user from outside the housing. However, it is also possible to attach the selection element (17) in a concealed position as described above or also to attach it to the inside of the lancet device. In the design shown as an example in FIG. 1 the selection element is located at a position in which it cannot be accidentally actuated at the same time as other operating elements of the lancet device (10). This especially applies in the case of one-handed operation of the lancet device.

The lancet device (10) shown as an example in FIG. 1 additionally has a trigger element (15) designed as a push-button or press switch. The puncturing movement of the respectively selected lancet can be triggered by actuating the trigger element (15). The lancet device shown additionally has an operating element (14) projecting from the housing (11) at the distal end (10b) of the lancet device (10). The lancet drive described above that is not shown in FIG. 1 can be tensioned by actuating the operating element (14). The lancet drive can for example be tensioned by a rotational movement of the operating element around the main axis of rotation of the lancet device (10) or for example also by sliding the operating element (14) towards the proximal end (10a) of the lancet device.

The operating elements of the lancet device (10) shown as an example in FIG. 1 are advantageously located at positions on the user interface that are spatially separated from one another. In the design that is shown, the selection element (17) although being at the same height as the trigger element (15), is located in a position diametrically opposed thereto which substantially prevents a simultaneous actuation when it is operated using one hand. This arrangement would be especially advantageous for a lancet device where the magazine is advanced immediately before a puncturing movement i.e. during the tensioning of the lancet drive. This effect could for example be further assisted if the selection element (17) were mounted on a recessed position of the operating interface.

Figure 2:
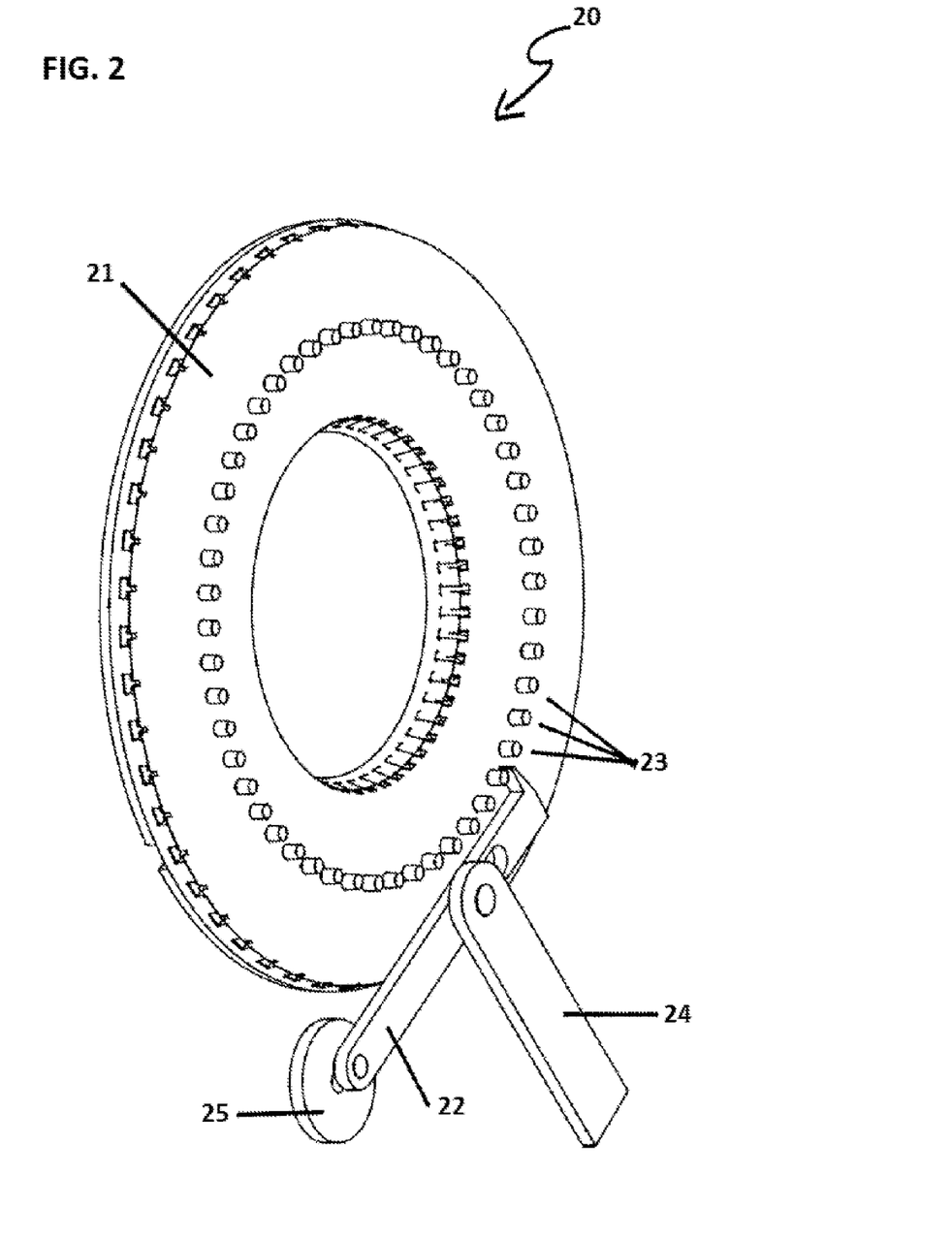
FIG. 2 is a perspective view of a step-switching mechanism with a lancet magazine that can be used.

A step-switching mechanism (20) of exemplary embodiments of the lancet device (10) is shown as an example in FIG. 2. In the design that is shown the body to be moved or rotated is a circular disk-shaped lancet magazine (21). The upper side of the lancet magazine (21) carries a plurality of counter elements (23) which are arranged in a circle and concentrically to the magazine (21). Alternatively it is, however, also possible that the counter elements (23) of the step-switching mechanism are not, as described above, directly attached to the lancet magazine (21) but rather to a magazine carrier which can be mechanically firmly but detachably joined to a lancet magazine.

The step-switching mechanism shown in FIG. 2 additionally has a movable gripper (22). This can be brought into mechanical engagement with the counter elements (23) mounted on the magazine (21) by a constantly uniform movement. This allows the periodic translatory movement of the gripper to be converted into a stepped rotation of the body to be rotated designed as a disk magazine (21) as shown in FIG. 2. The constantly uniform backwards and forwards movement of the gripper (22) can for example be accomplished by a suitable rotating drive (25).

The step-switching mechanism (20) shown as an example in FIG. 2 additionally has a control element (24) that is mechanically linked to the movable gripper (22). The control element (24) shown is arranged such that it can temporarily shift the spatial arrangement of the movable gripper (22) in such a manner that it can no longer engage with the counter elements (23) of the body to be rotated. This ensures that despite the continuation of the uniform movement of the gripper (22), the body to be rotated which in this case is the lancet magazine (21) that is shown is no longer rotated further as envisaged in the passive operating state of the lancet device. The active operating state can be re-established from this passive operating state in which, despite the continuing movement of the gripper (22), the lancet magazine (21) is no longer advanced for example after actuating the actuating element (14), by shifting the control element (24) into the initial state. In this active operating state the movable gripper (22) is located in a position in which it engages during its uniform recurring movement with the counter elements (23) of the step-switching mechanism (20).

Figure 3A:
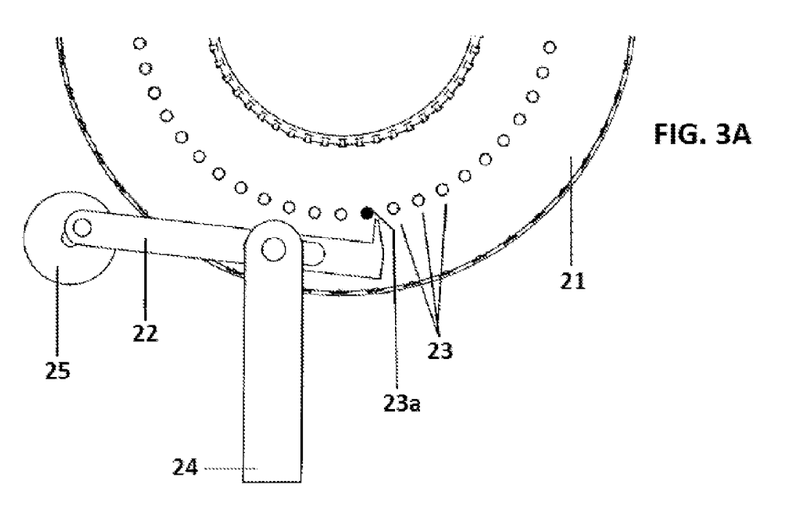
FIGS. 3A to 3E show the step-switching mechanism from FIG. 2 in the active operating state (movable gripper in engagement with counter elements).
Figure 3B:
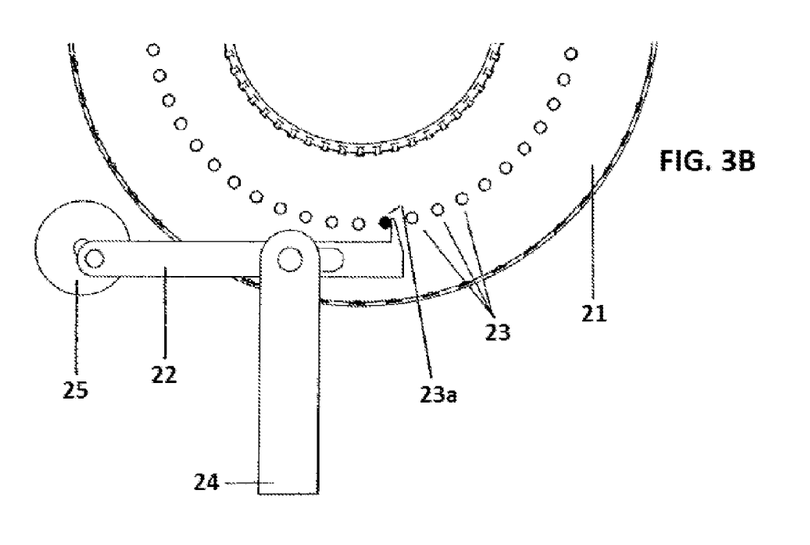
Figure 3C:
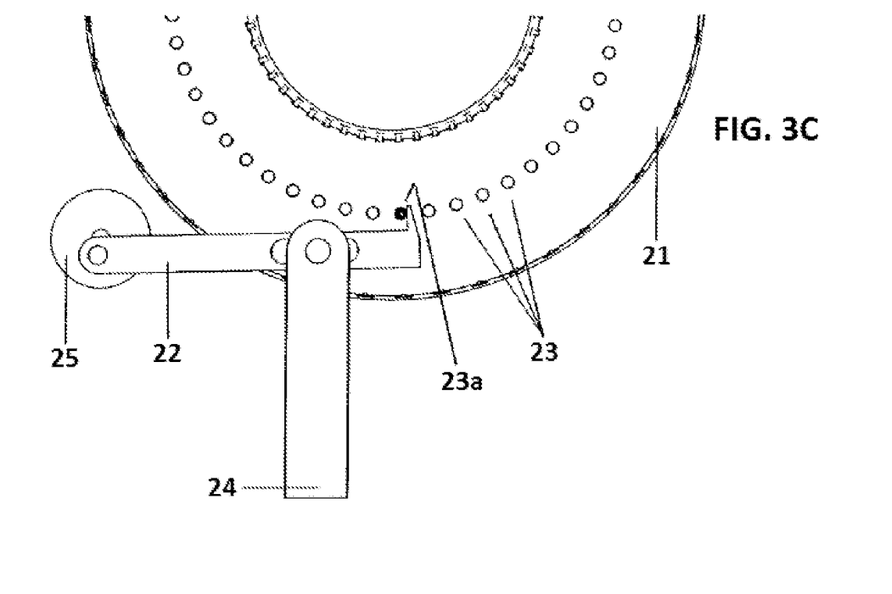
Figure 3D:
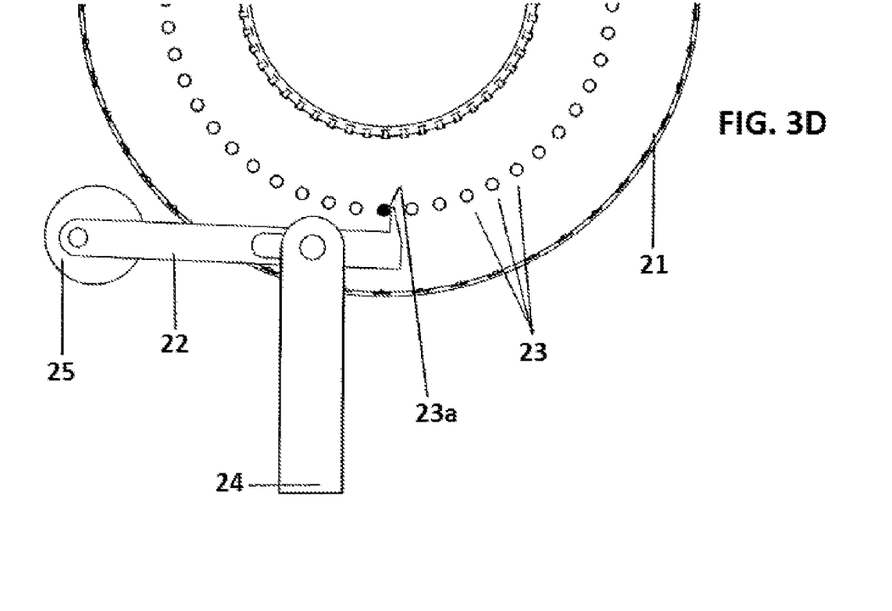
Figure 3E:
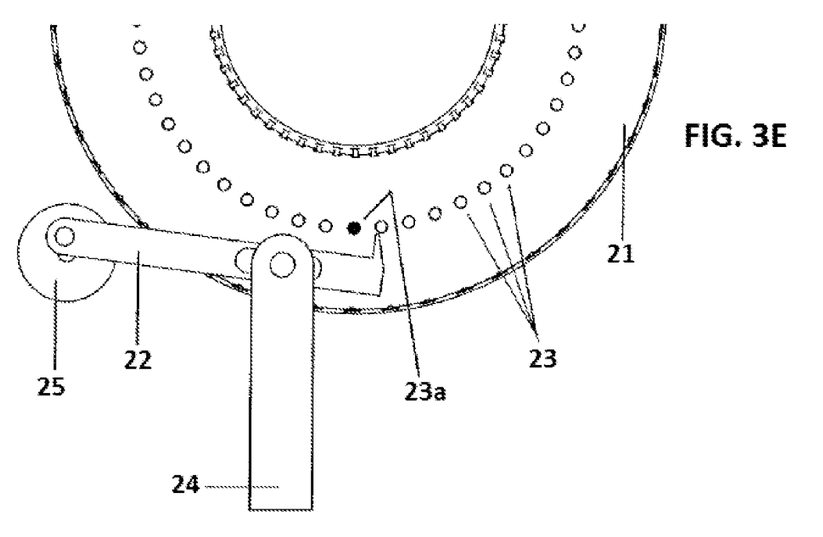
Figure 4A:
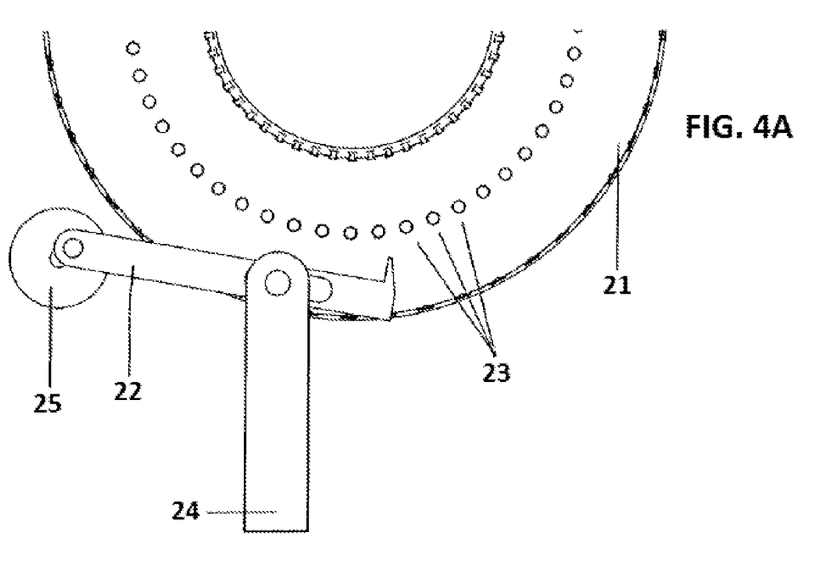
FIGS. 4A to 4E show the step-switching mechanism from FIGS. 2 and 3 in the passive operating state (movable gripper disengaged).
Figure 4B:
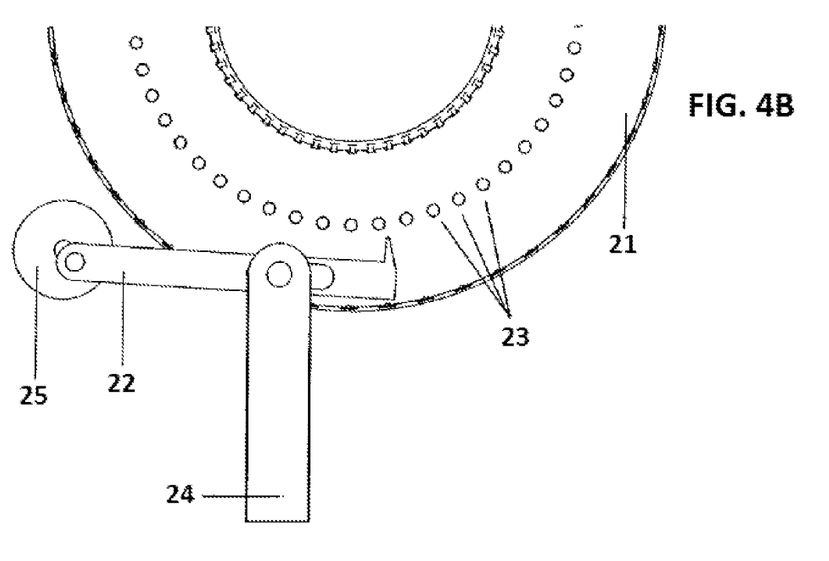
Figure 4C:
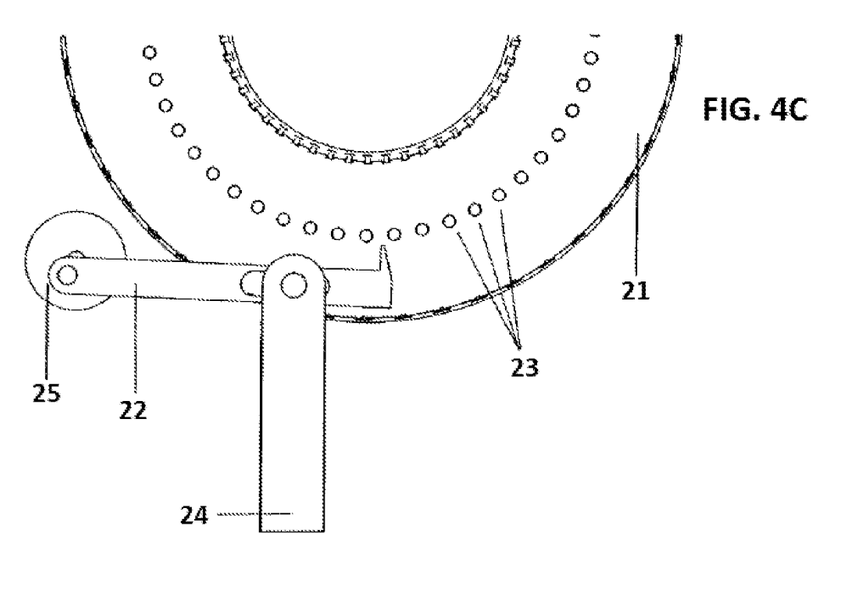
Figure 4D:
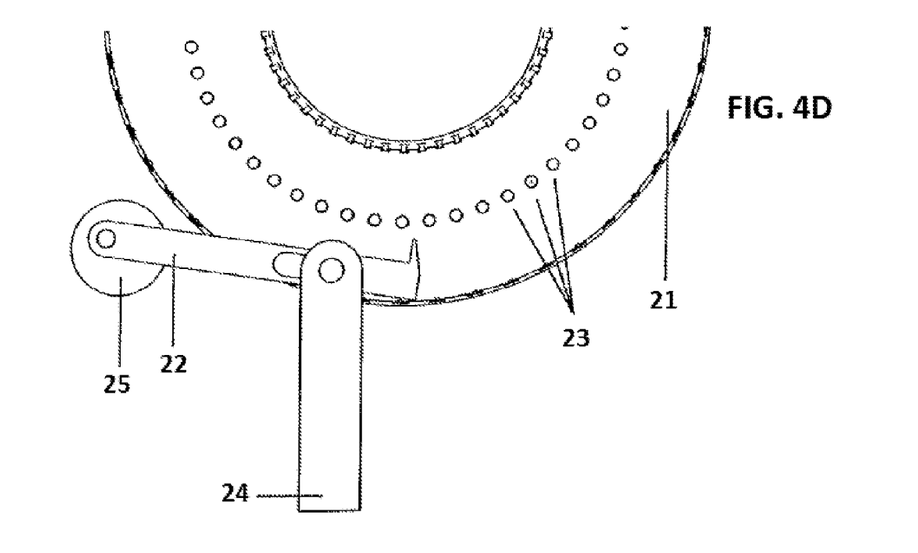
Figure 4E:
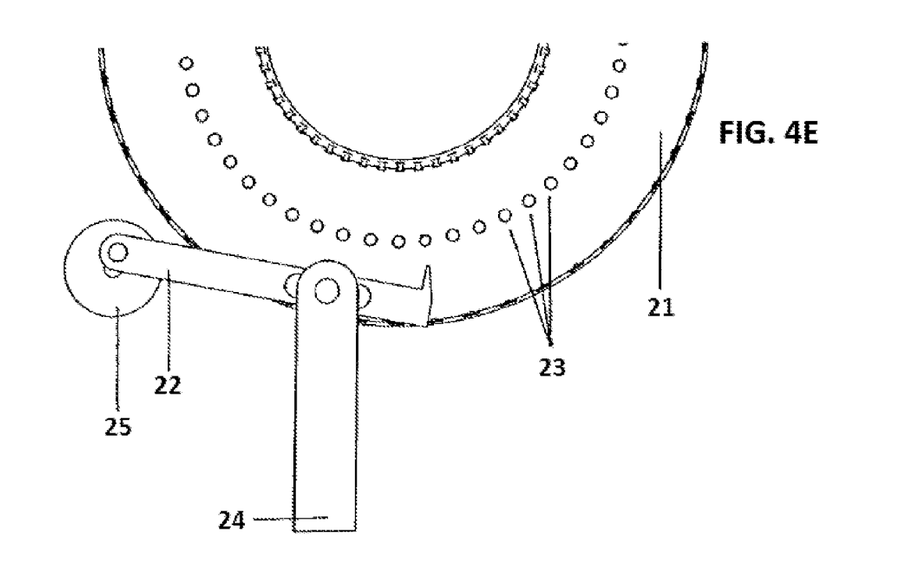

The motion sequence of the step-switching mechanism (20) shown as an example in the active operating state is shown in FIGS. 3A to 3E. FIG. 3A represents the starting point of the motion sequence. Here the gripper (22) is shifted by the control element (24) towards the disk magazine (21) such that it can engage with the counter elements (23). This situation is shown in FIG. 3B where the gripper (22) has tilted towards the counter elements (23) of the step-switching mechanism by a clockwise rotation of the drive (25) and comes into contact with the counter element (23a) that is marked for illustration. As shown in FIG. 3C, further rotation of the drive (25) moves the gripper towards the lower edge of the figure and in doing so picks up the counter element (23a) that is in contact with the gripper (22). This results in a clockwise rotation of the disk magazine (21) up to the situation shown in FIG. 3D in which the direction of movement of the gripper (22) reverses resulting in a subsequent loss of contact with the counter element (23a). This is shown in the final FIG. 3E in which the gripper (22) is positioned before making contact with the next counter element or, depending on the construction, before it comes into contact with one of the next counter elements (23). This enables the periodic recurring movement of the gripper to be converted into a uniform stepped rotation i.e. into an advance of the lancet magazine.

In contrast FIGS. 4A to 4E show the analogous motion sequence of the step-switching mechanism (20) in the passive operating state. In this case the position of the gripper (22) is shifted so far from the disk magazine (21) by sliding the control element (24) that the gripper (22) does not come into contact with one of the counter elements (23) over the entire recurring sequence of motion. As a result even the continued movement of the gripper (22) does not lead to a rotation or an advance of the lancet magazine.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS 10 lancet device with a proximal end (10a) and distal end (10b)
11 housing with user interface
12 cap
13 exit opening of the housing
14 actuating element (tensioning button)
15 trigger element
16 fastening clip
17 selection element
20 step-switching mechanism
21 lancet magazine
22 movable gripper
23, 23a counter elements
24 control element
25 drive

What is claimed is:

1. A lancet device for producing a puncture wound, comprising:
 a magazine holder for holding a lancet magazine having several lancets;
 a lancet drive with a drive spring, a tensioning device for tensioning the drive spring and a connecting element adapted to contact a lancet arranged in the lancet magazine and move the lancet in a puncturing movement to produce a puncture wound;
 a magazine advancing mechanism configured to advance the lancet magazine to successively bring the lancets stored therein into a position in which they can be contacted by the connecting element and moved by the connecting element in a puncturing movement, the magazine advancing mechanism having active and passive operating states;
 a selection element with which the magazine advancing mechanism can be selectively shifted into the active or passive operating state, the magazine advancing mechanism remaining in the selected operating state until the selection element is shifted to the other respective operating state;
 wherein, in the active operating state the magazine advancing mechanism automatically advances the lancet magazine before or after a puncturing movement of a lancet and causes an unused lancet of the lancet magazine to be brought into contact with the connecting element in the subsequent puncturing movement;
 further wherein, in the passive operating state the magazine advancing mechanism does not advance the lancet magazine before or after a puncturing movement of a lancet, whereby, in the subsequent puncturing movement the same lancet used in the previous puncturing movement is again brought into contact with the connecting element of the lancet drive.

2. The lancet device of claim 1, wherein the connecting element is configured to couple to and move with a lancet located in the lancet magazine to make a puncturing movement.

3. The lancet device of claim 1, wherein the connecting element comprises a push rod.

4. The lancet device of claim 1, wherein the selection element can reversibly shift the magazine advancing mechanism into the active or passive operating state.

5. The lancet device of claim 1, wherein the magazine advancing mechanism can only be shifted from one of the two operating states into the other respective operating state during actuation of the selection element.

6. The lancet device of claim 1, wherein the magazine advancing mechanism is mechanically coupled to the lancet drive in the active operating state.

7. The lancet device of claim 1, wherein in the active operating state the magazine advancing mechanism is coupled to the tensioning device and the lancet magazine is advanced during actuation of the tensioning device to tension the drive spring.

8. The lancet device of claim 1, wherein the lancet advancing mechanism comprises a step-switching mechanism.

9. The lancet device of claim 8, wherein the step-switching mechanism comprises a movable gripper and several counter elements, the movable gripper being arranged to engage the counter elements to advance the lancet magazine.

10. The lancet device of claim 9, wherein the movable gripper is a component of the lancet device.

11. The lancet device of claim 9, wherein the counter elements are components of the lancet magazine.

12. The lancet device of claim 9, wherein the magazine holder comprises a movable magazine carrier and the counter elements are a component of the movable magazine carrier.

13. The lancet device of claim 9, wherein, in the passive operating state of the magazine advancing mechanism the movable gripper does not engage the counter elements.

14. A lancet device for producing a puncture wound, comprising:
   a magazine holder configured to hold a lancet magazine having several lancets;
   a lancet drive comprising a drive spring, a tensioning device for tensioning the drive spring and a connecting element which contacts and moves a lancet located in the lancet magazine in a puncture movement; and
   a magazine advancing mechanism for advancing the lancet magazine to successively bring the lancets stored therein into a position in which they can be contacted by the connecting element and moved by the connecting element in a puncturing movement, the magazine advancing mechanism having an active state in which the lancet magazine is automatically advanced before or after a puncture movement and a passive state in which the magazine advancing mechanism is deactivated to allow multiple puncture movements with the same lancet without advancing the lancet magazine, wherein in the active state, the magazine advancing mechanism is mechanically coupled to a drive of the device and in the passive state the magazine advancing mechanism is decoupled from the drive.

15. The lancet device of claim 14, further comprising a selection element with which the magazine advancing mechanism can be selectively shifted into the active or passive operating state.

16. The lancet device of claim 15, wherein after actuating the selection element to select an operating state, the magazine advancing mechanism remains in the selected operating state until the other respective operating state is selected by further actuation of the selection element.

17. The lancet device of claim 15, wherein the magazine advancing mechanism can only be shifted from one of the two operating states into the other respective operating state by actuation of the selection element.

18. The lancet device of claim 14, wherein the magazine advancing mechanism is mechanically coupled to the lancet drive in the active operating state.

19. The lancet device of claim 14, wherein the lancet advancing mechanism comprises a step-switching mechanism.

20. The lancet device of claim 19, wherein the step-switching mechanism comprises a movable gripper and several counter elements, the movable gripper being arranged to engage the counter elements to advance the lancet magazine.

21. The lancet device of claim 20, wherein, in the passive operating state of the magazine advancing mechanism the movable gripper does not engage the counter elements.

22. The lancet device of claim 14, wherein the drive to which the magazine advancing mechanism is coupled in the active state is the lancet drive.

23. The lancet device of claim 22, wherein in the active operating state, the magazine advancing mechanism is coupled to the tensioning device and the lancet magazine is advanced during actuation of the tensioning device to tension the drive spring.

\* \* \* \* \*